United States Patent
Iaizzo et al.

(10) Patent No.: US 6,671,550 B2
(45) Date of Patent: Dec. 30, 2003

(54) SYSTEM AND METHOD FOR DETERMINING LOCATION AND TISSUE CONTACT OF AN IMPLANTABLE MEDICAL DEVICE WITHIN A BODY

(75) Inventors: Paul A. Iaizzo, White Bear Lake, MN (US); Timothy G. Laske, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 140 days.

(21) Appl. No.: 09/953,485

(22) Filed: Sep. 14, 2001

(65) Prior Publication Data

US 2002/0042632 A1 Apr. 11, 2002

Related U.S. Application Data

(60) Provisional application No. 60/234,058, filed on Sep. 20, 2000, and provisional application No. 60/256,630, filed on Dec. 18, 2000.

(51) Int. Cl.$^7$ ............................................... A61N 1/362
(52) U.S. Cl. ............................................................ 607/27
(58) Field of Search ................................ 600/528, 586; 607/1–28

(56) References Cited

U.S. PATENT DOCUMENTS

| | | |
|---|---|---|
| 2,702,354 A | 2/1955 | Chorpening |
| 4,351,345 A | 9/1982 | Carney |
| 4,444,195 A | 4/1984 | Gold |
| 4,591,668 A | 5/1986 | Iwata |
| 4,608,993 A | 9/1986 | Albert |
| 4,821,723 A | 4/1989 | Baker, Jr. et al. |
| 4,924,877 A | 5/1990 | Brooks |
| 4,947,852 A | 8/1990 | Nassi et al. |
| 5,078,148 A | 1/1992 | Nassi et al. |
| 5,085,628 A | 2/1992 | Engebretson et al. |
| 5,131,388 A | 7/1992 | Pless et al. |
| 5,144,949 A | 9/1992 | Olson |
| 5,158,078 A | 10/1992 | Bennett et al. |
| 5,179,962 A | 1/1993 | Dutcher et al. |
| 5,199,428 A | 4/1993 | Obel et al. |
| 5,312,453 A | 5/1994 | Shelton et al. |
| 5,314,430 A | 5/1994 | Bardy |
| 5,330,507 A | 7/1994 | Schwartz |
| 5,331,966 A | 7/1994 | Bennett et al. |
| 5,333,614 A | 8/1994 | Feiring |
| 5,348,019 A | 9/1994 | Sluss, Jr. et al. |
| 5,354,316 A | 10/1994 | Keimel |
| 5,387,233 A | 2/1995 | Alferness et al. |
| 5,396,902 A | 3/1995 | Brennen et al. |
| 5,427,144 A | 6/1995 | Teets et al. |
| 5,456,654 A | 10/1995 | Ball |
| 5,526,820 A | 6/1996 | Khoury |
| 5,545,186 A | 8/1996 | Olson et al. |
| 5,554,096 A | 9/1996 | Ball |
| 5,578,068 A | 11/1996 | Laske et al. |
| 5,728,149 A | 3/1998 | Laske et al. |
| 5,873,835 A | 2/1999 | Hastings et al. |
| 5,888,187 A | 3/1999 | Jaeger et al. |
| 6,006,137 A | 12/1999 | Williams |
| 6,064,905 A | 5/2000 | Webster, Jr. et al. |
| 6,174,278 B1 | 1/2001 | Jaeger et al. |
| 5,873,835 C1 | 8/2001 | Hastings et al. |

FOREIGN PATENT DOCUMENTS

| | | |
|---|---|---|
| GB | 2 213 381 A | 8/1989 |
| WO | WO 93/09725 | 5/1993 |

*Primary Examiner*—Scott M. Getzow
(74) *Attorney, Agent, or Firm*—Girma Wolde-Michael; Daniel G. Chapik

(57) ABSTRACT

The current invention provides an improved system for monitoring status of an IMD within a body. The system includes a device such as a lead, guidewire, stylet, catheter, or other IMD carrying a device such as a microphone for detecting acoustic signals in the body. The IMD is coupled to an amplifier device which generates an audible signal that may be utilized to determine status associated with the IMD, including location and tissue-contact data. A processing circuit may further be provided to aid in the analysis of the acoustic data.

32 Claims, 7 Drawing Sheets

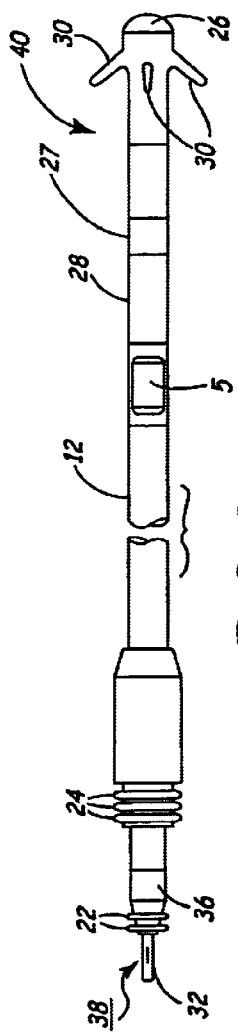
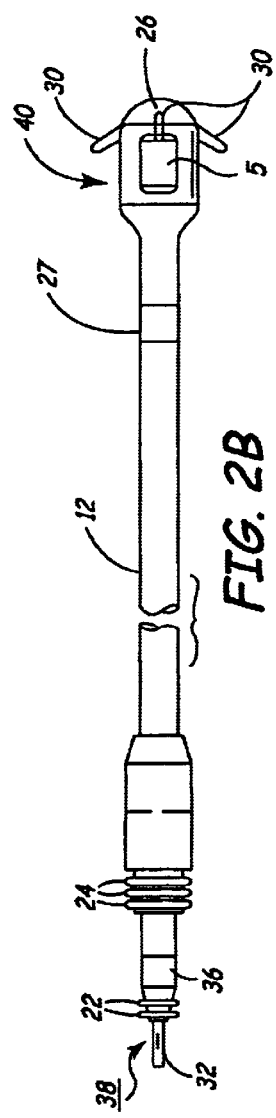
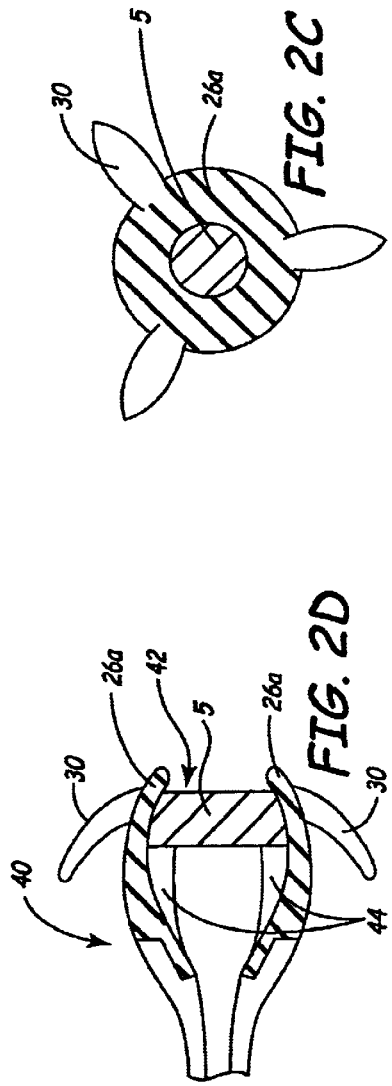
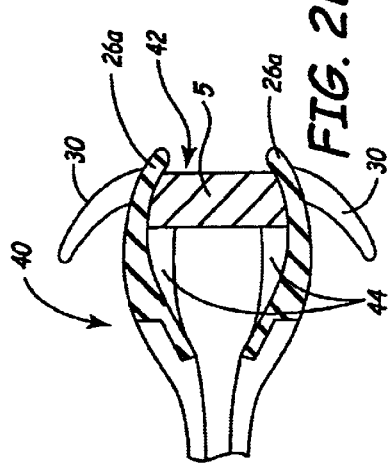

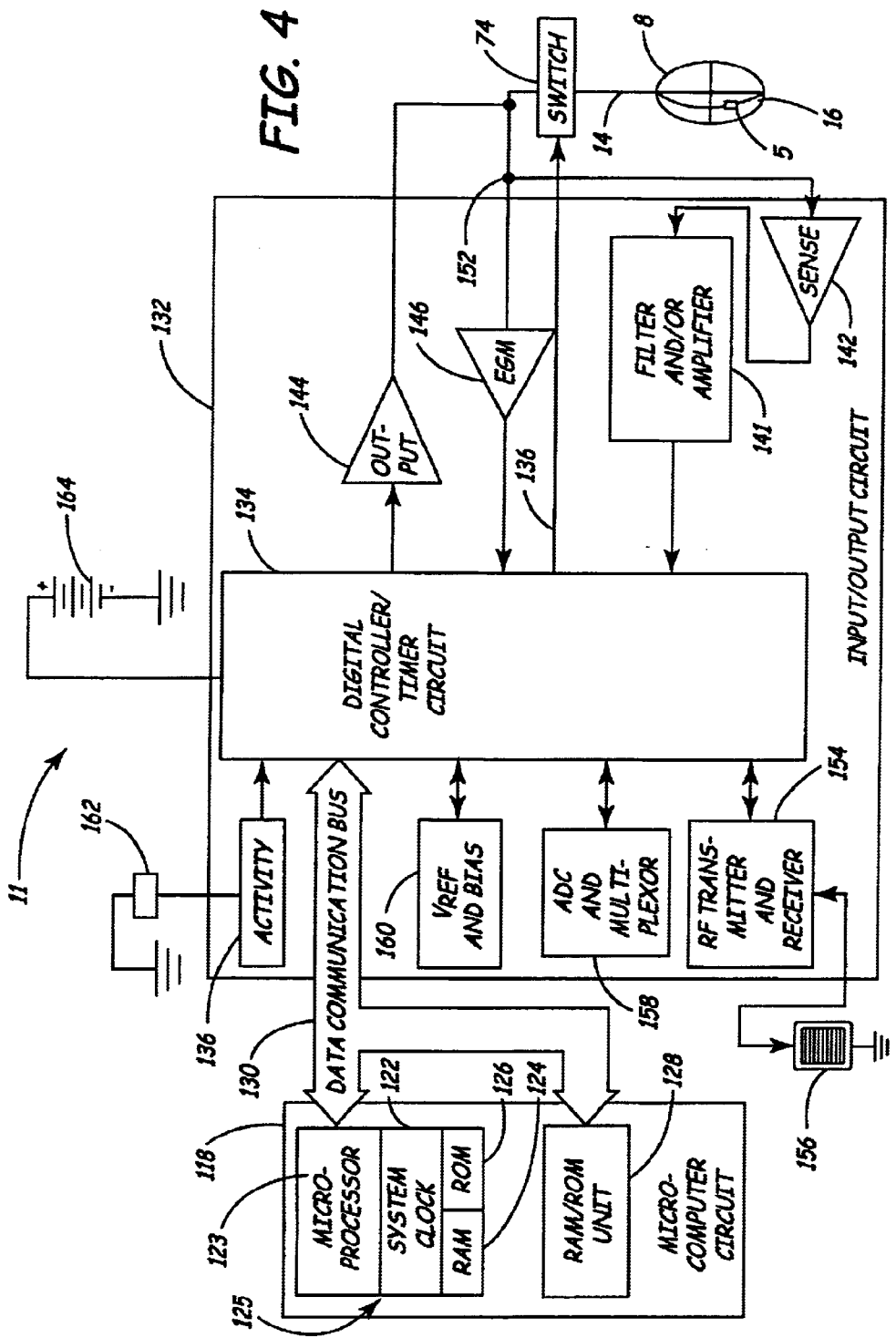

SYSTEM AND METHOD FOR DETERMINING LOCATION AND TISSUE CONTACT OF AN IMPLANTABLE MEDICAL DEVICE WITHIN A BODY

RELATED APPLICATIONS

This application claims priority to provisionally-filed patent application serial No. 60/234,058 filed Sep. 20, 2000, and further to provisionally-filed patent application serial No. 60/256,630 filed Dec. 18, 2000, which is incorporated herein by reference in its entirety.

FIELD

This invention relates generally to a system and method for placing leads within a body; and more particular, relates to the use of audio signals for determining lead location and for assessing the level of tissue contact achieved by one or more devices carried on the lead.

BACKGROUND OF THE INVENTION

Implantable medical electrical leads have long been employed in the fields of cardiac stimulation and monitoring. For example, leads are generally employed to deliver electrical stimulation for cardiac pacing and cardioversion/ defibrillation applications. In these applications, endocardial leads are placed through a transvenous route to locate one or more sensing and/or stimulation electrodes in a desired location within a heart chamber or interconnecting vasculature. To provide effective therapy, electrodes carried at the lead distal end need to be accurately positioned at a predetermined location against the endocardium or within the myocardium. The lead distal tip is then generally affixed by a passive or active means to the tissue to maintain the desired locations.

It is often difficult to determine whether a lead has been properly positioned and adequate tissue contact has been achieved. In some instances, catheters and leads are utilized that include materials that will allow for visualization with fluoroscopy. Additionally, fluoro-visible dyes may be injected into the cardiac chambers and venous anatomy so that the chambers of the heart and the related vasculature are visible using a fluoroscopic device. This procedure, sometimes referred to as a "venogram", allows the surgeon to locate a precise site and achieve proper electrode placement when performing an implant procedure.

Although the use of fluoro visible media is viable in some instances, this process has several disadvantages. First, some patients have adverse physical reactions when exposed to the fluoro visible dye used to obtain a venogram. Moreover, obtaining the venogram exposes the patient and clinicians to radiation. Additionally, a fluoroscope of the type needed for obtaining the fluoro-visible image may not be available. Finally, obtaining the venogram adds additional steps to the implant procedure, lengthening the time required to complete the procedure and increasing the risk of infection and complications to the patient.

What is needed, therefore, is an alternative system and method for placing, and otherwise monitoring the status of, an implantable medical device within the vascular system of the body without the need to inject a fluoro visible media into the body.

SUMMARY OF THE INVENTION

The current invention provides an improved system for monitoring status of an IMD within a body. The system includes a device such as a lead, guidewire, stylet, catheter, or other IMD carrying a device such as a microphone for detecting acoustic signals in the body. The IMD is coupled to an amplifier device which, in one embodiment, may be provided by a stand-alone device or included within an external programmer. An electrical representation of the measured acoustic signal is provided by the IMD to the amplifier device so that an audible signal may be generated by the amplifier device. A trained user can utilize the pitch and other characteristics of the audible signal to determine status associated with the IMD. Because unique patterns are associated with the acoustic signals that may be measured at distinct points within the cardiovascular system, the pitch of the audible signal may be used to determine the location of the acoustic measuring device, and thus, the IMD, within the body. Other information may be gained from the audible signal, including the extent of any contact between the IMD and tissue, and/or the extent of fixation of the IMD to tissue.

In one embodiment of the invention, the amplifier device includes a processing circuit to analyze the audible signal. For example, the processing circuit may compare the sensed audible signals to stored patterns. This comparison may then be used to determine IMD status, including location and tissue contact data. The processing circuit may provide this status information to an output device such as a printer or display monitor. According to one aspect of the invention, a virtual image of the IMD within the body may be generated using the status information.

The IMD of the current invention may include a switch mechanism. This switch mechanism may be used to selectively couple signals generated by the acoustic measurement device to a connector of the IMD during an implant procedure. This switch is re-configured during normal IMD operation so that other sensing devices such as electrodes are coupled to the connector. Use of this type of switching mechanism allows a standard connector, or alternatively, a non-standard connector having minimal connector contacts, to be utilized by the IMD.

The IMD may further include additional physiological sensors such as pressure, temperature, flow velocity, flow acceleration, and electrical activity sensors to provide additional physiological signals measured within the cardiovascular system to the amplifier device. This data may be utilized to confirm, or to further enhance, the status data that is generated using the acoustic signals.

In one embodiment of the invention, the amplifier device is included within a second IMD such as a pacemaker, cardioverter/defibrillator, drug pump, or any other implantable medical device rather than an external device. Periodic acoustic measurements are provided by the first IMD, which may be a lead, to the second IMD. This may involve configuring an electronic switch included within the lead to make the signals available to the second IMD. These acoustic signals may then be used by the second IMD to detect dislodgement or detachment of the first IMD, or to analyze a patient's condition. In response to the sensing of a predetermined patient condition, the second IMD may issue an alert or modify therapy delivery. The acoustic data may further be stored as trend data that may be used by a clinician in evaluating long-term patient condition. Other aspects of the current invention will become apparent to those skilled in the art from the drawings and accompanying description.

BRIEF DESCRIPTION OF THE DRAWINGS

FIG. 2A is a side view of one embodiment of a lead that may carry a microphone or another similar device for detecting sound waves.

FIG. 2B is a side view of alternative embodiment of a lead for use with the current invention.

FIG. 2C is an end view of yet another embodiment of a distal end of a lead for use with the current invention.

FIG. 2D is a side cutaway view of the embodiment of FIG. 2C.

FIG. 4 is a block diagram of an implantable medical device (IMD) as may be used with the current inventive lead system.

DETAILED DESCRIPTION OF THE INVENTION

Figure 1:
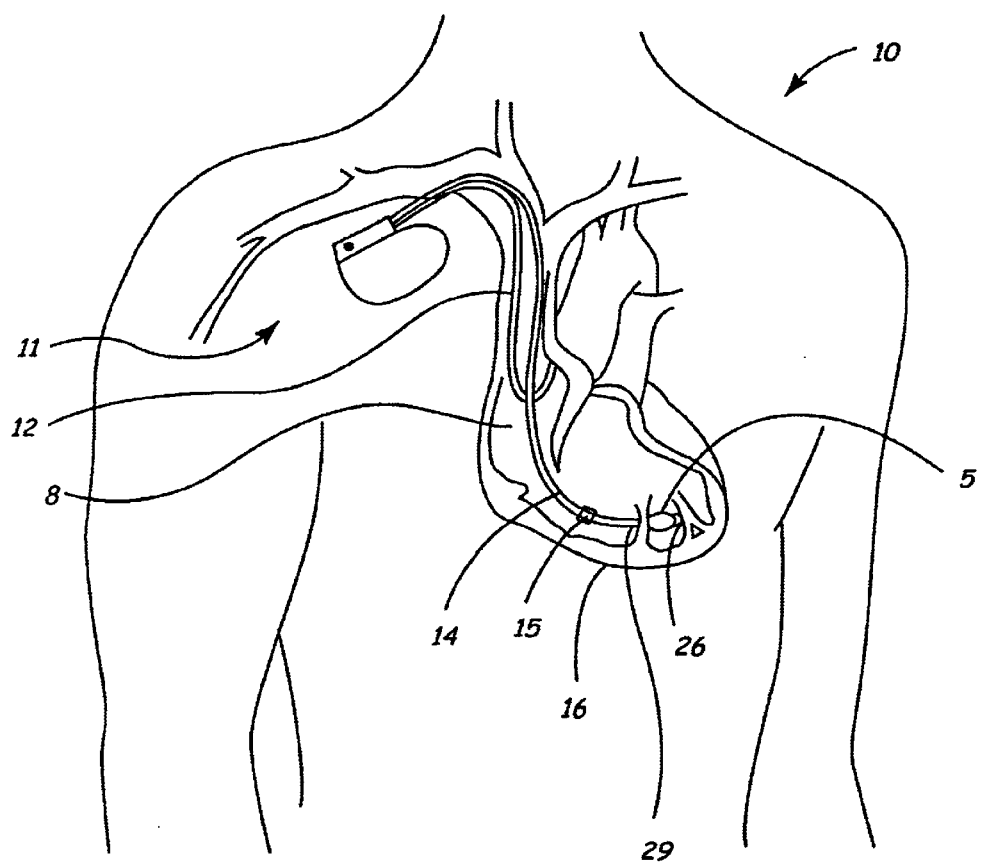
FIG. 1 is a diagram illustrating an implantable medical device (IMD) system implanted within a body of a patient.

FIG. 1 is a diagram illustrating an implantable medical device (IMD) system implanted within a body of a patient. The system includes a device for detecting sound waves shown as microphone 5. The microphone may be attached to, or integrally formed as a component of, lead 14, or another type of IMD, as will be discussed below. In the case of a lead, the lead may be unipolar or bipolar, and may be adapted to operate in cooperation with a wide variety of implantable medical devices.

Lead 14 is positioned in heart 16 of patient 10, and is attached to IMD 11, shown implanted in the upper right chest of patient 10. The lead 14 may include any of the passive or active fixation mechanisms known in the art. For example, lead distal tip 27 may include a tined tip. Lead may further include one or more electrodes, such as a tip electrode 26. Tip electrode senses electrical signals attendant to the depolarization and repolarization of heart 16, and may also transmit pacing pulses for causing depolarization of cardiac tissue in the vicinity of the electrode. Lead may further include a ring electrode, one or more high-voltage electrodes, and/or one or more additional sensors such as sensor 15. The use of these additional sensors is discussed further below.

IMD 11 may be an implantable cardiac pacemaker, such as of the types disclosed in U.S. Pat. No. 5,158,078 to Bennett et al., U.S. Pat. No. 5,312,453 to Shelton et al., or U.S. Pat. No. 5,144,949 to Olson, hereby incorporated herein by reference in their respective entireties. IMD 11 may also be a pacemaker-cardioverter-defibrillator (PCD), such as any of those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker et al. At least some of the devices disclosed in the foregoing patents may be employed in conjunction with the present invention. In yet another embodiment, IMD 11 may be an implantable nerve stimulator or muscle stimulator, such as those disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device, such as that disclosed in U.S. Pat. No. 5,331,966 issued to Bennet et al. The IMD may alternatively be a hemodynamic monitor or a drug pump. In general, IMD 11 is encased in a hermetically-sealed enclosure that may include various circuit elements to be discussed in more detail below.

As discussed above, lead 14 is shown to include microphone 5. This microphone may be any type of microphone suitable for implantation within a living body. For example, implantable microphones used with implantable electromagnetic hearing transducers may be employed, as described in U.S. Pat. Nos. 5,554,096 and 5,456,654 to Ball, and U.S. Pat. No. 5,085,628 to Engebretson et al. Additional exemplary microphone designs are disclosed by Iwata in U.S. Pat. Nos. 4,591,668, 2,702,354 to Creed et al., and U.S. Pat. Nos. 5,888,187 and 6,174,278 to Jaeger et al.

FIG. 2A is a side view of one embodiment of a lead that may carry microphone 5 or another similar device for detecting sound waves. Lead includes an elongated lead body 12 which may be formed of silicone, polyurethane, or any other biocompatible polymer known in the art for use in implantable devices.

Lead body 12 has a proximal end 38 adapted to be coupled to an IMD. Proximal end may include two sets of sealing rings 22 and 24 to provide a fluid-tight seal with the IMD connector. The lead further includes a connector pin 32 and connector ring 36. Although the lead connector of FIG. 2 is a bipolar in-line configuration, any other type of standard or non-standard connector type may be utilized.

The lead body 12 has a distal end 40, which may carry a tip electrode 26, and may also carry a ring electrode 27. Any type of passive or active fixation mechanism may be utilized if desired, including tines 30 or a fixation helix. Distal end 40 further carries a microphone 5 or another similar device for detecting sound waves.

In this embodiment, the lead body 12 carries first and second lead conductors, which may be cabled or coiled conductors, or any other type of configuration known in the art. During implantation, a selectable switch is configured to couple connector pin 32 and ring connector 36 to microphone 5 via these conductors. When coupled to a speaker system in a manner to be discussed below, the microphone may then be used to facilitate lead placement. After placement has been accomplished, the switch may be reconfigured so that connector pin 32 is coupled to tip electrode 26, and ring connector 36 is coupled to ring electrode 27. The use of the microphone during lead placement will be discussed in detail below.

FIG. 2B is a side view of alternative embodiment of a lead for use with the current invention. In this embodiment, microphone 5 is located in proximity to tip electrode 26.

FIG. 2C is an end view of yet another embodiment of a distal end of a lead for use with the current invention. In this embodiment, tip electrode 26a is provided with an aperture that provides access to a recessed area that houses microphone 5.

FIG. 2D is a side cutaway view of the embodiment of FIG. 2C. This view illustrates the manner in which the microphone 5 is mounted within recessed area 42 to mounting structures 44. This may be accomplished, for example, using medical grade epoxy or any other fastening means.

Turning now to a discussion of lead placement, techniques currently in use for permanent lead implantation typically involve making an infraclavicular incision in the skin on either the left or right side of the patient. The left or right subclavian vein is punctured with a thin-walled, large-bore needle. A guidewire may then be passed into the vein. The needle is removed and an introducer sheath is advanced over the wire with the aid of a dilator into the subclavian vein. After the introducer sheath is in the subclavian vein, the dilator is withdrawn. The lead is passed into the venous circulation system through the introducer sheath. The guidewire may be removed or may be left in place as the lead is passed through the system. Alternatively, a guide catheter may be used in place of, or in addition to, a guide wire during lead placement. The guide catheter is navigated through the venous system to a desired implant location. Once the distal tip of the guide catheter is in position, the lead is advanced within the guide catheter lumen.

Regardless of the technique used, the lead may be advanced via the superior vena cava into the right atrium and then manipulated across the tricuspid valve into the right ventricle, then further advanced past ventricular trabeculae to the apex of the right ventricle to obtain an optimal pacing location in the right ventricle.

In some instances, it is desirable to place a lead within the coronary sinus. The coronary sinus is the largest cardiac vein in the heart and serves as a venous conduit from smaller veins within the myocardium to the right atrium. The coronary sinus can be used as a location for pacing both the left and right sides of the heart, and is often accessed to provide electrophysiology therapy. Gaining access to the ostium of the coronary sinus is a very difficult procedure, however, especially because of the large number of similar anatomical structures located near the coronary sinus within the right atrium. The location of these structures varies from patient-to-patient, and can not be readily viewed using a fluoroscope.

Current procedures available for introduction of leads within the chambers of the heart as well as the venous system are frequently time consuming and difficult. As discussed above, these procedures may be aided by obtaining an image of the interior anatomy of a patient. This is commonly accomplished by injecting fluorovisible contrast media into a patient's system so that the image may be generated by a fluoroscope. This procedure has disadvantages, including exposing patients to the contrast media, which may cause temporary side effects, as well as exposing patients to radiation.

According to the current invention, an improved procedure utilizing sound wave analysis is provided to aid in the positioning of implantable medical devices within a patient's body. A microphone attached to a lead captures the various sound waves generated by a body, including sounds created by the flow of blood through the veins and arteries, as well as the audible tones created by atrial and ventricular contractions. The frequency and amplitude of the sound waves vary as the microphone travels through the body. In fact, a unique acoustic pattern or signature may be obtained at various locations in the body. This allows a trained user to very accurately estimate the location of a distal tip of a lead by listening to the sounds received by a microphone carried on the lead body.

Figure 3:
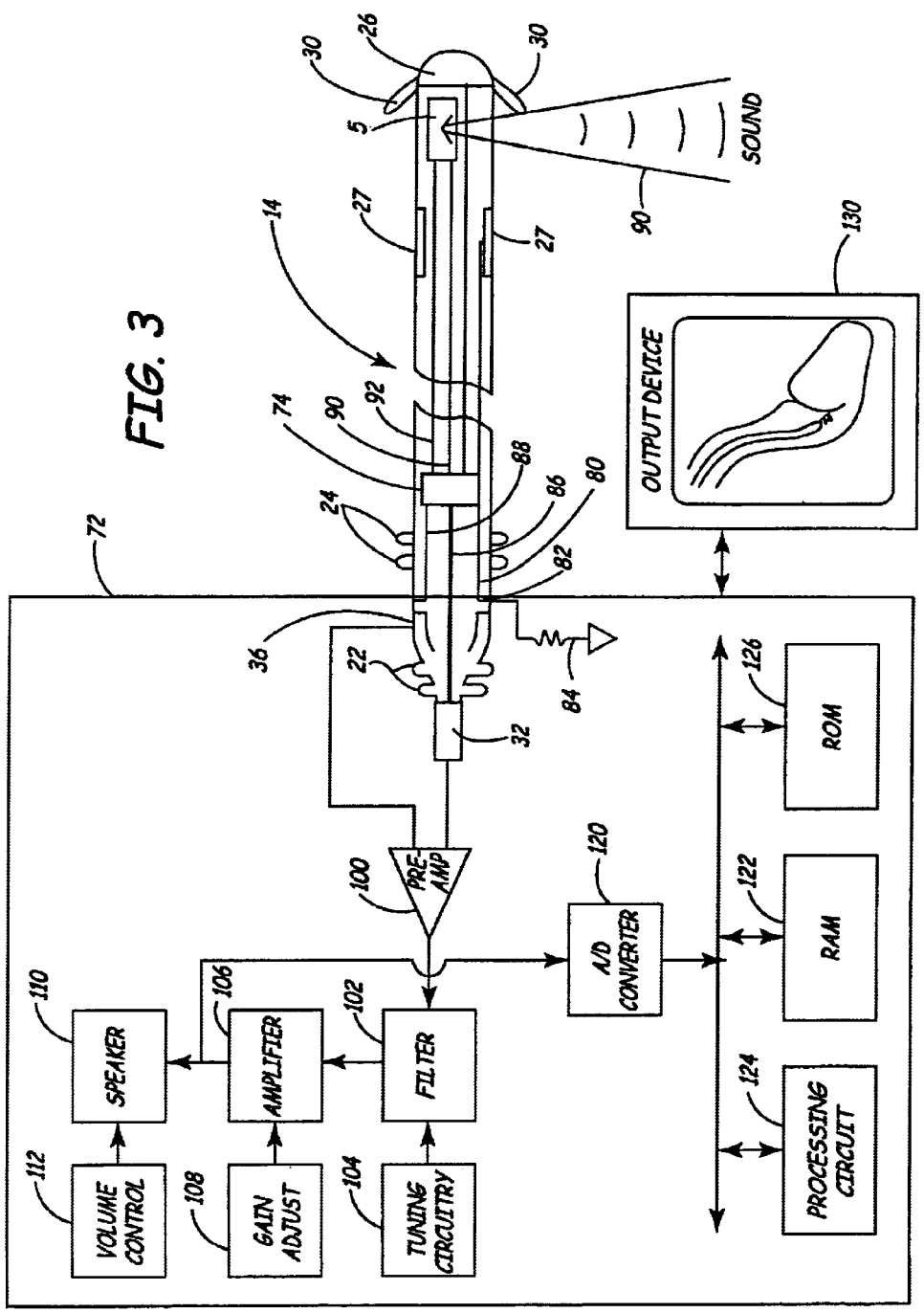
FIG. 3 is a block diagram of a system that utilizes sound waves to aid in the positioning of a lead within a patient's body during an implantation procedure.

FIG. 3 is a block diagram of a system that utilizes sound waves to aid in the positioning of a lead within a patient's body during an implantation procedure. This system includes lead 14, which may be any of the embodiments shown in FIGS. 2A–2D. The exemplary lead is similar to that shown in FIG. 2B, with similar components being labeled with like numerical designations. This lead is electrically and mechanically coupled to an amplifier device 72 for amplifying sound waves received by microphone 5 located at the distal end of the lead.

In one embodiment of the invention, the lead body carries a switch 74. This switch, which selectively couples the lead connectors 86 and 88 to either the microphone 5 or the various lead electrodes, may be a mechanical switch accessible to an external surface of the lead and configured manually by a user. Alternatively, the switch may be an electronic switch such as a multiplexer shown in FIG. 3 that is configured by a control line 80. Control line 80 is coupled via an additional connector ring 82 at the proximal end of lead 14 to resistor network 84 within amplifier device 72, and is thereby maintained at an appropriate voltage level, which in this instance is shown to be ground.

Before an implantation procedure is initiated, the lead proximal end is coupled to the amplifier device 72 and switch 74 is configured so that conductors 90 and 92 couple microphone 5 to pin connector 32 and ring connector 36, respectively, of the lead via conductors 86 and 88. As discussed above, if switch 74 is a multiplexer, switch configuration will occur automatically when control line 80 is pulled to a predetermined voltage level after being coupled to amplifier device 72.

After the switch is configured, the lead distal tip is introduced into the patient's body. Placement of the lead may be aided by a guidewire and/or guide catheter. As the distal tip 40 of lead 14 is navigated through the venous system and heart chambers, sound waves 90 are received by microphone 5. The microphone converts the sound waves to an electrical signal, which is transmitted between conductors 90 and 92 to conductors 86 and 88, and finally to the pin connector 32 and ring connector 36 of the lead. This signal is electrically transmitted via conductors within amplifier device 72 to pre-amplifier circuit 100. Pre-amplifier circuit amplifies the electrical signal, which is then provided to filter 102. Filter 102 eliminates noise from the signal. A filter for use with the current invention will be selected to pass signals having a frequency within a predetermined portion of the audio range. The filter may be adjustable using tuning circuitry 104, which selects the retained range of frequencies.

The filtered signal is provided to amplifier circuit 106, which may have an adjustable gain that is controlled by gain adjustment circuitry 108. The amplified signal is provided to speaker 110. Speaker generates an audible signal indicative of sound waves 90 as controlled by volume control 112. To a trained ear, the audible signal will distinctly indicate the position of the microphone within the body so that lead placement can be facilitated more easily. For example, direct contact of a valve leaflet with an endocardial microphone will produce a distinct acoustic pattern identifiable by the user. The audible signal can be used to locate the coronary sinus ostium, or to pin-point lead distal tip location within an atrial or ventricular chamber of the heart. Moreover, the extent of lead fixation at the distal tip can be determined by a change in audible signal as a fixation mechanism such as tines 30 are embedded within the heart wall. The audible tones can also be used to detect lead dislodgement, as may occur when a guide catheter is removed from the body after lead placement has been completed. Furthermore, these tones can be used for long-term monitoring and diagnostic purposes. For example, audible tones will change with the accumulation of fluid in the patient's system, as generally occurs when a patient becomes ischemic. This tonal change can be used to detect the on-set of such conditions so that appropriate therapy may be provided.

In one embodiment of the invention, the signal generated by amplifier circuit 106 is provided to an analog-to-digital (A/D) converter 120. The digital signal may be stored in Random Access Memory (RAM) 122, or received directly by processing circuit 124. Processing circuit 124, under the control of microcode stored in RAM 122 and/or Read-Only Memory (ROM) 126, may compare the digitized audio signals to audio signatures stored in RAM and/or ROM. These stored signatures may represent typical audio signatures at various locations in a patient's body. Based on this comparison between the measured audio signals and the stored signatures, an approximate location of microphone 5 within the body may be determined. This approximate location data can be provided to an output device 130 for use by the clinician. Output device 130 of FIG. 3 is shown to be a display which generates a virtual image of the approximate location of the microphone 5, as well as the rest of lead 14. Alternatively, the processing circuit 124 may provide the location information to another type of output device, such as a printer, an LED display, or any other type of user interface.

The audio signatures used for comparison purposes may vary from patient to patient based on physiological characteristics, including a patient's size, weight, health conditions, and so on. Therefore, in one embodiment of the invention, these signatures can be selected based on these characteristics. The selected signatures may be downloaded to RAM prior to initiation of the implant procedure. In another embodiment, audio signatures may be obtained directly from a patient during a previously-completed mapping procedure. In such a procedure, the position of an implanted flouro-visible microphone is varied within the patient's body. The audio signature is recorded at each location within the body. At the same time, the precise location as determined by a flouroscope is also stored along with the corresponding signature. This audio map may be stored in a patient profile and downloaded to amplifier device 72 during any subsequent implant procedure to accurately place a lead or another implantable device.

It may be appreciated that many different embodiments of amplifier device 72 are possible within the scope of the current invention. For example, pre-amplifier circuit 100 may not be included in some embodiments. In other embodiments, the speaker 110 and/or volume control may be provided as a separate device. Similarly, optional display 130 may be incorporated into amplifier device 72, or may be omitted entirely from the system. Alternatively, the processing circuit 124, A/D converter 120, and memory may be provided along with display 130 as a separate device or omitted entirely.

Further, it may be appreciated that many alternative embodiments of the lead system may be used with the current invention. For example, if additional connectors are provided on the lead proximal end so that dedicated connectors are available for transmitting the signal received from the microphone 5, switch 74 may be omitted. Additionally, the lead may include more or fewer electrodes.

FIG. 4 is a block diagram of an implantable medical device (IMD) as may be used with the current invention. IMD may be of any type of implantable device known in the art, including any of those discussed above. The exemplary device shown in FIG. 4 is pacemaker 11 electrically coupled to patient's heart 16 by lead 14. Stimulation may be provided to heart 16 via output circuit 144 under the control of digital controller/timer circuit 134. Similarly, cardiac signals may be sensed by EGM amplifier circuit 146. Controller/timer circuit 134 also provides a control line 136 to control the configuration of switch 74 (FIG. 3) carried by lead 14 in a manner to be discussed below.

IMD 11 further includes microcomputer unit 118. This unit may include on-board circuit 125 comprising microprocessor 123, system clock 122, and on-board RAM 124 and ROM 126. In this illustrative embodiment, an off-board circuit 128 comprises a RAM/ROM unit. On-board circuit 125 and off-board circuit 128 are each coupled by a data communication bus 130 to digital controller/timer circuit 134. Electrical components are powered by an appropriate implantable battery power source 164 in accordance with common practice in the art. Antenna 156 is connected to input/output circuit 132 to permit uplink/downlink telemetry with an external device through RF transmitter and receiver unit 154. Transmitter/Receiver unit 154 may correspond to the telemetry and program logic disclosed in U.S. Pat. No. 4,566,063 issued to Thompson et al. Voltage reference (VREF) and bias circuit 160 generates a stable voltage reference and bias current for the analog circuits of input/output circuit 132. Analog-to-digital converter (ADC) and multiplexer unit 158 digitize analog signals and voltages to provide "real-time" intracardiac signals and battery end-of-life (EOL) replacement signals that may be stored in memory or transmitted to an external device such as a programmer.

Operating commands for controlling the timing of pacemaker 11 are coupled by data bus 130 to digital controller/timer circuit 134, where digital timers and counters establish the overall escape interval of the pacemaker as well as various refractory, blanking, and other timing windows for controlling the operation of the peripheral components disposed within input/output circuit 132.

As discussed above, in addition to providing timing and control signals that control the delivery of therapy, digital controller/timer circuit 134 also provides a control signal on line 200 that configures switch 74 (FIG. 3.) During normal operation, switch is configured via the signal on line 136 so that electrodes carried by lead 14 are coupled to input/output circuit 132 in the manner discussed above. However, during periodic intervals, switch 74 may be temporarily configured by changing the voltage level on signal line 136 so that microphone 5 is coupled electrically to sense amplifier 142. Acoustic signals sensed by microphone 5 are amplified and/or filtered by circuit 141 and provided to controller/timer circuit 134. These signals may be digitized by ADC circuit 158, and thereafter stored in RAM 124 or RAM/ROM unit 128. The processor may compare these signals to stored audio patterns or signatures to determine whether lead dislodgment has occurred. If such dislodgment is detected, an audible alert may be generated, or a warning message may be transmitted via RF transmitter/receiver circuit 154.

As discussed above, changes in the audio signals can also be used to detect a change in a patient's long-term condition. Digitized audio signals may be periodically stored in memory to diagnose trends. Changes over time may signal such conditions as the on-set of ischemia, for example. If such conditions are detected, a warning may be provided so that appropriate therapy may be prescribed and delivered. Alternatively, a therapy may be automatically administered by changing the pacing regimen, for example.

Although the foregoing example discusses the use of a bipolar medical electrical lead, many other embodiments of the system are possible. For example, a microphone may be included in a drug delivery catheter, a guide catheter, a stylet, a guidewire, a unipolar lead, a lead for providing electrical stimulation to the nervous system, or any other type of implantable device that is navigated into position within a patient's body.

Figure 5A:
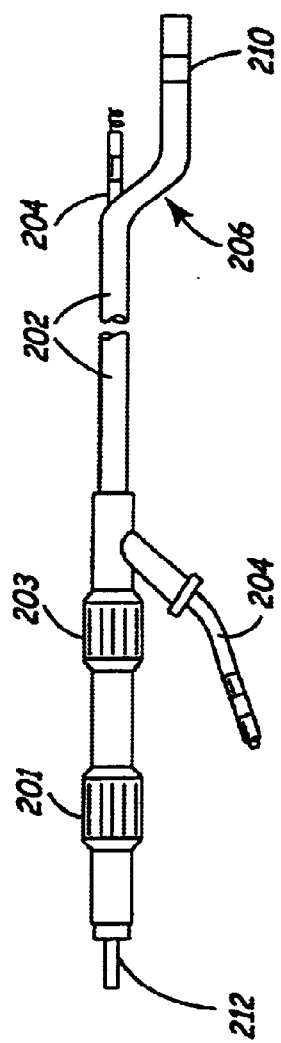
FIG. 5A is a side view of an exemplary deflectable guide catheter 200 as may be employed with the current invention.

FIG. 5A is a side view of an exemplary deflectable guide catheter 200 that may usefully employ the current invention. This guide catheter is described in detail in commonly-assigned U.S. Pat. No. 6,006,137 incorporated herein by reference in its entirety. It will be understood that this catheter design is merely exemplary, and any other deflectable or non-deflectable catheter design may usefully employ the current invention. This exemplary guide catheter has an elongated body 202 and a deflectable distal tip 206 controlled by several internal deflection wires coupled to two rotatable knobs 201 and 203. A medical electrical lead 204 is shown being advanced within an internal lumen of the guide catheter. The distal tip further carries a microphone 210 or another similar instrument for measuring sound waves. The proximal end of the guide catheter includes a connector 212 that can be coupled to amplifier device 72 in the manner discussed above. Acoustic waves received by microphone 210 can thereby be used to place the distal tip of the guide catheter so that a lead may be delivered at a predetermined location.

Figure 5B:
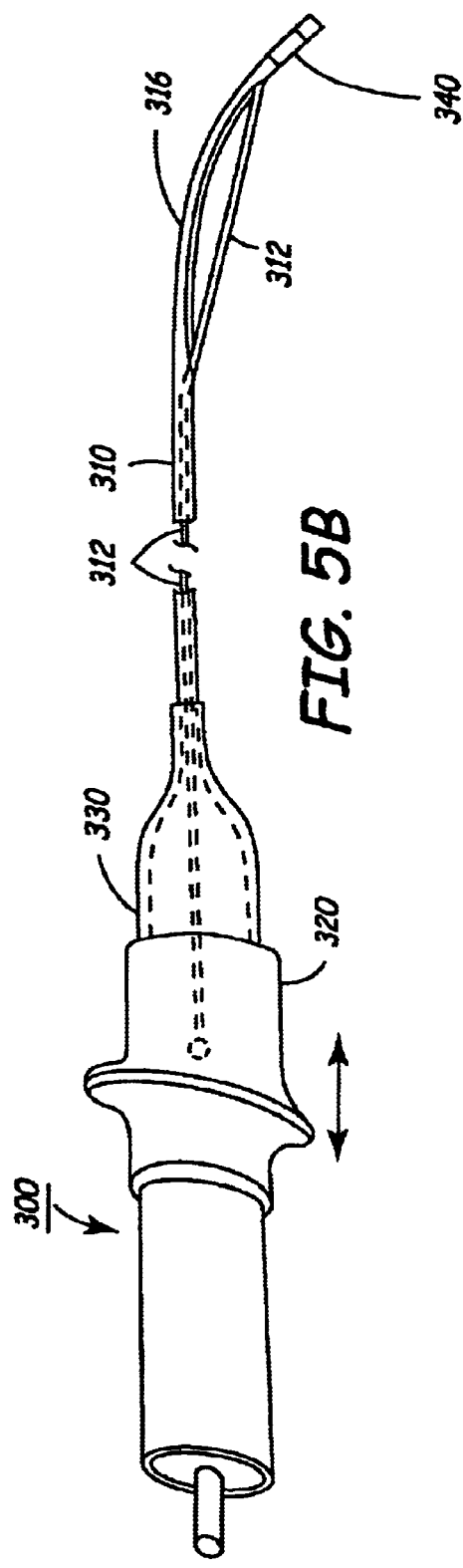
FIG. 5B is a perspective view of an exemplary steerable stylet that may be employed with the current invention.

FIG. 5B is a perspective view of an exemplary steerable stylet and manipulative handle assembly 300 as may be employed with the current invention. This stylet assembly is described in commonly-assigned U.S. Pat. No. 5,396,902 incorporated herein by reference. It will be understood that this stylet design is merely exemplary, and any other deflectable or non-deflectable stylet design may usefully employ the current invention. This style has a deflectable distal end 316 shaped via movement of pull wire 312 in relation to the elongated tubular member 310. In use, tubular member 310 and pull wire 312 are inserted into connector pin opening of a lead or catheter (not shown) and advanced into an inner lumen of the device. After this mechanical connection is effected, the lead or catheter may be rotated by rotation of housing 330, and curvature may be imparted by slide member 320 acting on pull wire 312. Distal tip of the stylet includes a microphone 340 to detect sound waves, which are converted to an electrical signal. Connector 350 is provided to couple to a device such as amplifier device 72 in a manner to discussed above so that the distal end of the stylet may be accurately positioned within the body.

The foregoing discussion focuses on the use of acoustic information to aid in determining location and/or tissue contact of an implantable device. Other types of sensors such as sensor 15 (FIG. 1) may be employed to gather additional information that may be used in conjunction with audio signal data to even more accurately determine the location of an IMD. For example, pressure data may be utilized to determine location of a pressure sensor. This is possible because intravascular pressure varies by location within the body in a manner similar to that discussed above with audible signals. For example, a distinct pressure shift may be detected as a pressure sensor enters the coronary sinus. Other pressure shifts occur as a sensor is moved from one cardiac chamber to the next. Therefore, a pressure sensor coupled to an IMD may be used to transfer signals to a device such as amplifier device 72 (FIG. 3). These signals may be digitized by A/D converter 120 and compared by processing circuit 124 to pressure signatures stored in RAM 122 or ROM 126 for use in determining the approximate the location of the pressure sensor in the body. This approximation may be used in conjunction with the analysis of the audio signals discussed above to even more accurately determine the location of the IMD. The sensor data may also be displayed on one or more output devices, as described above.

Any type of implantable pressure sensor may be adapted for use with the current invention. For example, commonly assigned U.S. Pat. No. 5,564,434 discloses an endocardial lead having a sensor to provide modulated pressure signals to an external monitor. Additional exemplary pressure sensing systems are disclosed in U.S. Pat. Nos. 5,526,820, 4,924,877, 5,427,144, and 5,348,019.

Other types of sensor data may be used in a manner similar to the pressure signals to further pin-point the location of an IMD. For example, sensors to measure flow velocities may be utilized to further determine location. Systems of this nature are discussed in U.S. Pat. Nos. 4,947,852, 5,078,148, 5,333,614, and 5,873,835. Another physiological parameter that may be used in conjunction with the current invention includes acceleration of blood flow, measurement of which is discussed in U.S. Pat. No. 4,608,993. Velocity and direction of electrical activity within myocardial tissue may also be measured to determine location, as discussed in U.S. Pat. No. 6,064,905.

Figure 6:
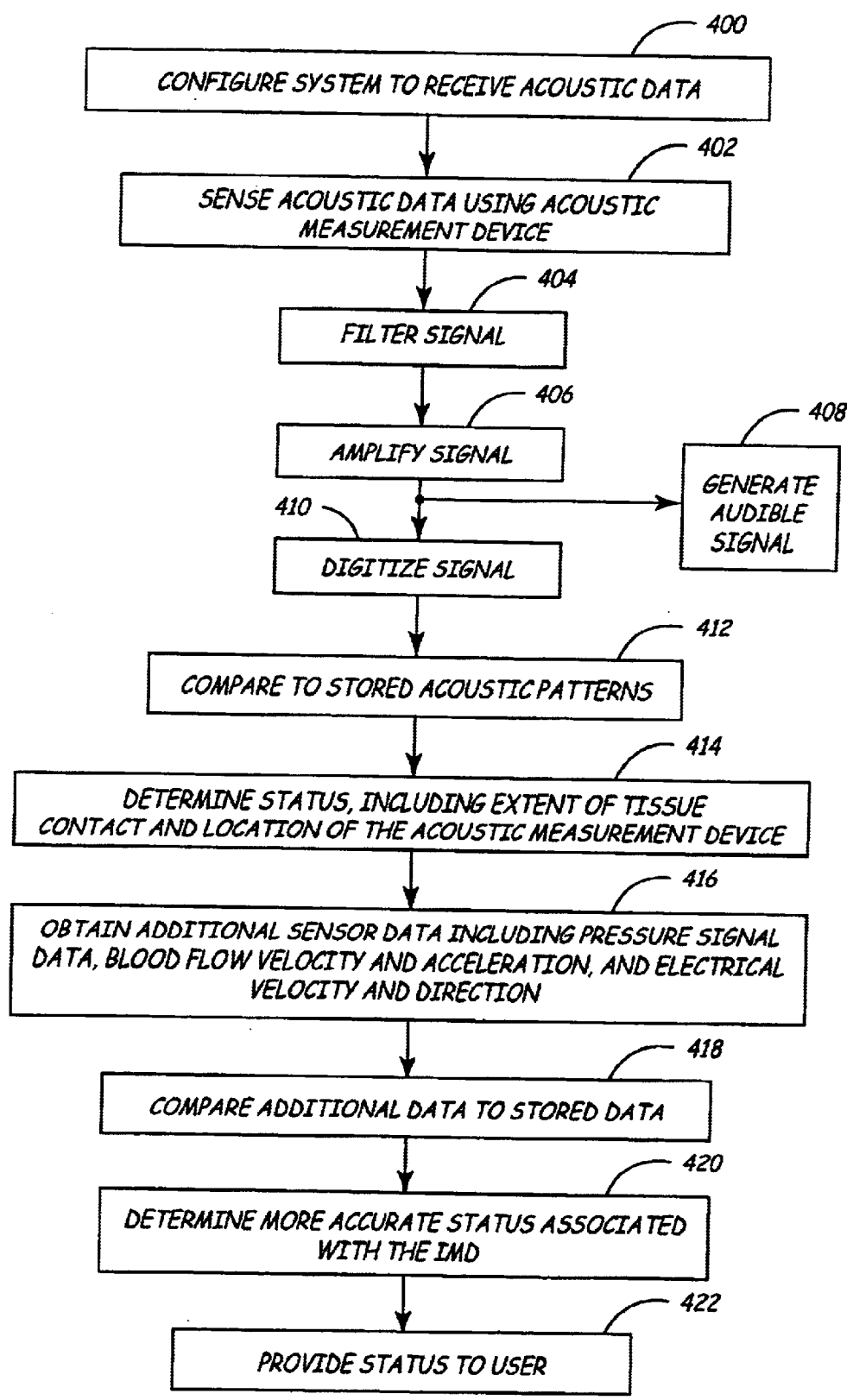
FIG. 6 is a flowchart of an exemplary process of obtaining status associated with an implantable medical device according to the current invention.

FIG. 6 is a flowchart of an exemplary process of positioning an implantable medical device according to the current invention. The system is first configured to receive acoustic data (400). This may involve setting a switch to a predetermined setting and/or connecting the IMD to the amplifier device. It may further involve loading acoustic pattern data into the amplifier device so that the acoustic analysis is tailored to an individual patient in the manner discussed above. Acoustic data may then be received by an acoustic measurement device such as a microphone (402). An electrical representation of the sensed acoustic data is filtered (404) and amplified (406). An audible signal may then be generated for use by a trained practitioner in determining position of the acoustic measuring device within a body (408).

Optionally, the filtered and amplified signal may be digitized (410) and compared to stored acoustic patterns as may be accomplished by a processing circuit under the control of microcode, for example (412). As noted above, the stored acoustic patterns may be tailored to reflect individual patient characteristics. Using the results of the comparison, status associated with the IMD may be determined (414). This status may include the approximate location of the acoustic measurement device within the body, as well as the extent of any contact between tissue and the acoustic measurement device.

If desired, one or more additional sensors such as sensor 15 (FIG. 1) may be utilized to obtain additional physiological measurements including pressure, blood flow velocity and acceleration, and the velocity and direction of electrical activity in myocardial tissue (416). These measurements may be received by amplifier device 72 and processed in a manner similar to that described above with respect to audio signals. For example, these signals may be filtered, amplified, and digitized. The digital signals may then be compared to pattern data stored in memory (418). The results of this comparison are used to even more accurately determine the status of an IMD, including IMD location (420). After the IMD status including location data is determined, the information is provided to a user. (422) For example, an image of the approximate location may be generated on a display device, or a printer may be utilized to provide the position information.

It may be noted that the ordering of the steps of FIG. 6 is in some cases arbitrary. For example, the order of filtering and amplification steps 404 and 406 may be reversed. Step 408 may be omitted, or alternatively, any of steps 410 through 422 may be omitted. Therefore, it will be understood that FIG. 6 is exemplary in nature, rather than limiting.

Figure 7:
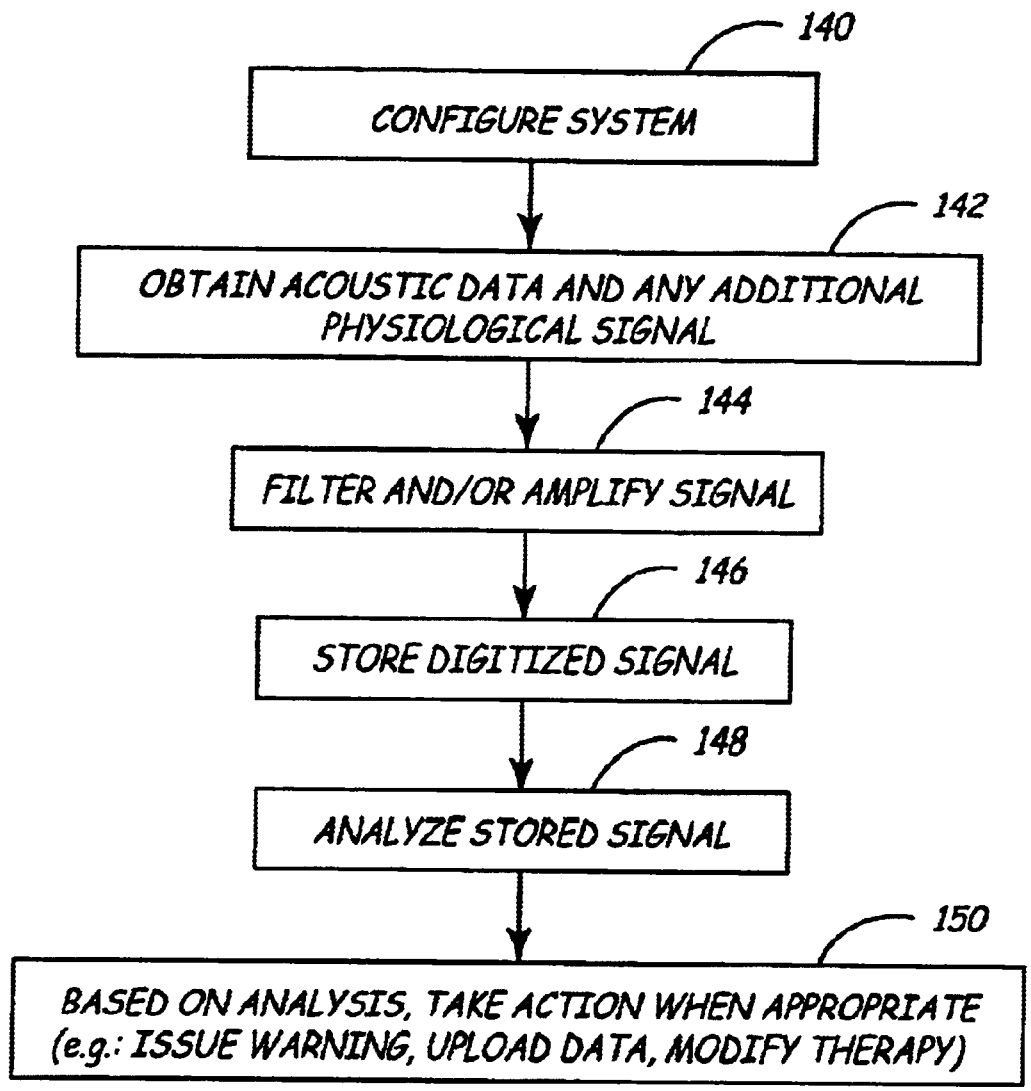
FIG. 7 is a flowchart of an exemplary process of utilizing the current invention to monitor long-term status of IMD implanted within a patient.

FIG. 7 is a flowchart of an exemplary process of utilizing the current invention to monitor long-term status of system such as a pacemaker coupled to one or more leads implanted within a patient. An exemplary system is shown in FIG. 4. According to this method of use, the system is configured to receive acoustic signals (440). This may involve configuring a switch such as switch 74 so that acoustic signals may be received by the pacemaker. After system configuration is completed, the acoustic data may be obtained using an acoustic sensing device such as a microphone. Optionally, other physiological data may also be obtained from one or more additional sensors such as a temperature, pressure, or any other sensor of a type known in the art (442).

After the acoustic and any other additional signal data is obtained, this data may be filtered and amplified (444). This data may further be digitized and sampled so that it may be stored in a storage device within the pacemaker (446). The sampled data may be analyzed by a processing circuit such as microprocessor 123 (448). This evaluation process may involve a rules-based analysis, and/or a comparison to stored pattern data, for example. After the analysis is complete, one or more additional actions may be taken (452). For instance, a warning may be generated to indicate the dislodgement of a lead or detachment of a fixation mechanism. Alternatively, the warning may indicate a worsening patient condition. This warning may be an audible alert, or may involve up-loading data to an external device such as a programmer. In one embodiment, the detection of a patient condition may result in the initiation or modification of therapy delivezy by the pacemaker or other IMD.

The above embodiments will be understood to be exemplary only. Those skilled in the art may contemplate variations within the scope of the present invention. The scope of the invention is therefore to be limited only in reference to the claims that follow.

What is claimed is:

1. A system for monitoring an implantable medical device (IMD) within a body, comprising:
    a first circuit to receive an electrical signal that is representative of an acoustic signal existing within a body; and
    a second circuit coupled to the first circuit to provide an audible signal from the received electrical signal for use in determining status associated with the IMD.

2. The system of claim 1, wherein the first circuit includes an amplifier circuit coupled to a filter circuit.

3. The system of claim 1, and further including a processing circuit to receive the electrical signal, and to utilize the electrical signal to generate an indication of IMD status.

4. The system of claim 3, wherein the processing circuit includes means for comparing the received electrical signal to predetermined acoustic patterns to generate an indication of IMD status.

5. The system of claim 4, and further including an output device coupled to receive the indication of IMD status from the processing circuit.

6. The system of claim 5, wherein the processing circuit includes means for generating a virtual image of the IMD on the output device.

7. The system of claim 4, wherein the processing circuit includes means for analyzing signals received from at least one additional physiological sensor for use in generating an indication of IMD status.

8. The system of claim 4, wherein the processing circuit includes means for determining approximate location of the IMD.

9. The system of claim 8, wherein the processing circuit includes means for determining tissue contact associated with the IMD.

10. An implantable medical device (IMD) within a patient, comprising:
    a measurement device to sense an acoustic signal; and
    a circuit coupled to the measurement device to determine, based on the acoustic signal, status indicative of a patient condition or status associated with the IMD, wherein the IMD includes a switch to selectively coupled the measurement device to the circuit.

11. An implantable medical device (IMD) within a patient, comprising:
    a measurement device to sense an acoustic signal; and
    a circuit coupled to the measurement device to determine, based on the acoustic signal, status indicative of a patient condition or status associated with the IMD, wherein the circuit includes a processing circuit to receive an indication of the acoustic signal and to thereby generate status indicative of the patient condition or the status associated with the IMD and the processing circuit includes means for determining contact between a portion of the IMD and tissue from the acoustic signal.

12. A system for use in providing therapy to a body, comprising:
    an implantable medical device (IMD) including a acoustic measurement device to receive acoustic waves transmitted within the body; and
    a second device coupled to the IMD to receive an indication of the acoustic waves, and to thereby provide data indicative of status associated with the IMD.

13. The system of claim 12, wherein the IMD includes at least one electrode and a switch to selectively couple either the acoustic measurement device or the at least one electrode to the second device.

14. The system of claim 12, wherein the IMD is selected from the group consisting of a catheter, a medical lead, a guidewire, and a stylet.

15. The system of claim 12, wherein the second device includes a processing circuit to process the indication of the acoustic waves, and to thereby generate data indicative of status associated with the IMD.

16. The system of claim 12, wherein the second device is a second implantable medical device.

17. The system of claim 16, wherein the second device includes a communication circuit to transmit the data indicative of status to an external device.

18. The system of claim 12, wherein the second device is a device located outside the body.

19. The system of claim 18, wherein the second device includes an output device to provide the data indicative of the status to a user.

20. The system of claim 19, wherein the second device is a display monitor to display a determined location of the IMD within the body.

21. A method of monitoring an implantable medical device (IMD) including an acoustic measurement device within a body, comprising the steps of:
    a.) utilizing the acoustic measurement device to sense acoustic signals within the body; and
    b.) determining status associated with the IMD based on an indication of the acoustic signals.

22. The method of claim 21, wherein step b.) includes determining a location of the acoustic measurement device within the body.

23. The method of claim 22, wherein the IMD includes at least one additional sensor for sensing physiological signals, and further including utilizing the sensed physiological signals to gain additional status associated with the IMD.

24. The method of claim 23, and further including utilizing the sensed physiological signals to confirm the location of the acoustic measurement device within the body.

25. The method of claim 21, wherein step b.) includes determining a degree of tissue contact between a portion of the IMD and the body.

26. The method of claim 21, wherein step b.) includes assessing a condition of the body based on the indication of the acoustic signals.

27. The method of claim 26, and further including providing a warning following assessing of the condition of the body.

28. The method of claim 21, and further including providing the status to an output device.

29. The method of claim 21, and further including creating an image of the IMD on a display device.

30. The method of claim 21, wherein step b.) includes comparing the indication of the acoustic signals to predetermined acoustic patterns to determine the status.

31. The method of claim 30, wherein the acoustic patterns are tailored to characteristics of the body.

32. The method of claim 21, wherein the IMD includes a switch coupled to the acoustic measurement device, and further including the step of selectively configuring the switch so that the acoustic measurement device may be utilized to determine the status.

* * * * *